United States Patent

Sasagawa et al.

[11] Patent Number: 5,609,743
[45] Date of Patent: Mar. 11, 1997

[54] ELECTROPHORESIS FRACTIONATOR

[75] Inventors: Tatsuru Sasagawa; Yutaka Fujii, both of Kamakura, Japan

[73] Assignee: Toray Research Center, Inc., Tokyo, Japan

[21] Appl. No.: 495,674
[22] PCT Filed: Nov. 29, 1994
[86] PCT No.: PCT/JP94/01999
   § 371 Date: Jul. 28, 1995
   § 102(e) Date: Jul. 28, 1995
[87] PCT Pub. No.: WO95/14923
   PCT Pub. Date: Jun. 1, 1995

[30] Foreign Application Priority Data

Nov. 29, 1993 [JP] Japan ................................ 5-298583

[51] Int. Cl.$^6$ ........................................................ G01N 27/26
[52] U.S. Cl. .................. 204/600; 204/606; 204/610; 204/613
[58] Field of Search .................... 204/606, 610, 204/613, 601, 605, 600, 644

Primary Examiner—Donald R. Valentine
Assistant Examiner—Alex Noguerola
Attorney, Agent, or Firm—Nikaido, Marmelstein Murray & Oram LLP

[57] ABSTRACT

An electrophoresis fractionator comprises a multiplicity of separate cells (10, 11) provided on respective contact surfaces of two members (1, 2) which are in contact with each other movably relative to each other and move relative to each other to enable alternate switching between a position where the multiplicity of cells (10, 11) are connected to a single electrophoresis passage P together and a position where the multiplicity of cells (10, 11) are separated from one another, and electrodes (14, 15) provided on both respective ends of the electrophoresis passage P which is formed to be single.

7 Claims, 6 Drawing Sheets

ELECTROPHORESIS FRACTIONATOR

TECHNICAL FIELD

The present invention relates to an electrophoresis fractionator capable of fractionating substances such as proteins mixed in an electrophoresis solution by electrophoresis to thereby separate the target substance.

BACKGROUND ART

Various means are now known for fractionating substances such as proteins according to their charges and molecular weights by electrophoresis and isolating the obtained fractions, which include a fractionation capillary electrophoresis apparatus, a preparative liquid electrofocusing apparatus and a method in which electrical separation is conducted in a gel and thereafter a desired substance is extracted from the gel. However, the above apparatus and method have the following drawbacks.

The fractionation capillary electrophoresis apparatus is one comprising a linear capillary of 1 mm or less in diameter provided with electrodes at its both ends, the separative power (capability of fractionation) of which is extremely high. However, the isolation of a substance separated by electrofocusing is conducted at the end of the capillary, so that it is required to push out the separated substance from the capillary. This operation gives an unfavorable influence such as disturbance of the separation pattern, thereby bringing about the disadvantage of rendering fractionation with high accuracy unfeasible. Further, the diameter of the capillary is as small as 1 mm or less that the amount of the sample subjected to electrophoresis is so small as to bring about a drawback in that the apparatus is unsuitable for use in the step of electrophoresis requiring a large amount of sample in one operation as in the structural analysis of, for example, an amino acid sequence.

The preparative liquid electrofocusing apparatus has such a construction that electrofocusing is performed in a cylinder having its inside partitioned into 20 sub-sections with membranes. Thus, electrophoresis is performed in an electrophoresis pipe partitioned into multiple sub-sections by suitable membranes, so that the diffusion of the separated substance is suppressed even after the discontinuation of the electrification with the result that this apparatus is free from the above noted drawbacks of the conventional fractionation capillary electrophoresis apparatus. However, the number of sub-sections is only 20, so that the separative power of the apparatus is relatively low to thereby bring about a drawback in that fractionation with high accuracy cannot be ensured. Moreover, this apparatus has the problem that the adsorption of proteins by the membranes, and the membrane clogging attributed to isoelectric precipitation, are detrimental to the separative power of the apparatus.

The above method in which the desired substance is extracted from a gel specifically comprises performing electrophoresis with the use of a gel prepared from, for example, polyacrylamide as an electrophoresis solution, staining the sample after the electrophoresis to thereby discriminate the desired substance, cutting out a portion of the gel containing the desired substance, and extracting the desired substance from the cut out gel portion. A sample as large as several milligrams can be processed depending on the gel size, and the separative power of the apparatus is relatively high. However, the step of extracting the desired substance separated by electrophoresis from the cut out portion of the gel is required, thereby posing the problems of a reduction in the extraction efficiency and contamination with impurities originating in the gel.

DISCLOSURE OF THE INVENTION

An object of the present invention is to provide an electrophoresis apparatus which ensures high separative power and realizes fractionation with high accuracy by simple operation.

Another object of the present invention is to provide an electrophoresis apparatus which can treat a large amount of sample in one electrophoresis operation.

The electrophoresis fractionator of the present invention, which is capable of attaining the above objects, comprises: a multiplicity of separate cells provided on respective contact surfaces of two members. These members are in contact with each other, are movable relative to each other, and are adapted to move relative to each other sufficient to enable alternate switching between a position where the multiplicity of cells are connected together to form a single electrophoresis passage and a position where the multiplicity of cells are separated from one another. Electrodes are provided on both respective ends of the thus formed unitary electrophoresis passage As mentioned above, the two movable members are adapted to enable alternate switching between a position where a multiplicity of cells are connected together to form a single electrophoresis passage and a position where the multiplicity of cells are spaced from one another sufficient to not form a single passage First, electrophoresis is carried out by filling the electrophoresis passage with an electrophoresis solution (carrier ampholyte) containing substances to be fractionated and in which the two members are positioned such that a multiplicity of cells are connected together to form a single electrophoresis passage. The above substances to be fractionated can be fractionated at the respective isoelectric positions. Subsequently, when the two members are moved to achieve switching to positions where at least some of the multiplicity of cells are separated from one another so as to not form a single passage the switching operation causes the substances fractionated in the respective isoelectric points to be separated and independently enclosed in the respective cells, so that a fractionation with high accuracy can be effected with respect to each of the cells.

Not only can the substances fractionated at the respective isoelectric points be isolated by the simple operation of merely moving the two members apart relative to each other, but also this can be effected irrespective of the size of the diameter of the electrophoresis passage with the result that a large amount of sample can be treated at one time.

Any substance, which is not particularly limited as long as electrophoresis is applicable thereto, can be fractionated by the electrophoresis fractionator of the present invention. That is, the above substances naturally include charged substances such as proteins. Further, even non-charged organic substances can be fractionated by adding a charged material, such as a surfactant, to each electrolytic solution to thereby bring the whole into a charged state. Dipeptides and higher polypeptides can be mentioned as examples of the proteins which can be electrophoretically resolved and then fractionated according to this invention.

The accuracy,of electrophoretic substances can be improved by the use of the electrophoresis fractionator of the present invention in combination with liquid chromatography. This enables not only fractionation of the contents of various cells, and DNA (deoxyribonucleic acid) separation, but also spermatzoon selection for selective fertilization.

BEST MODE FOR CARRYING OUT THE INVENTION

Figure 1:
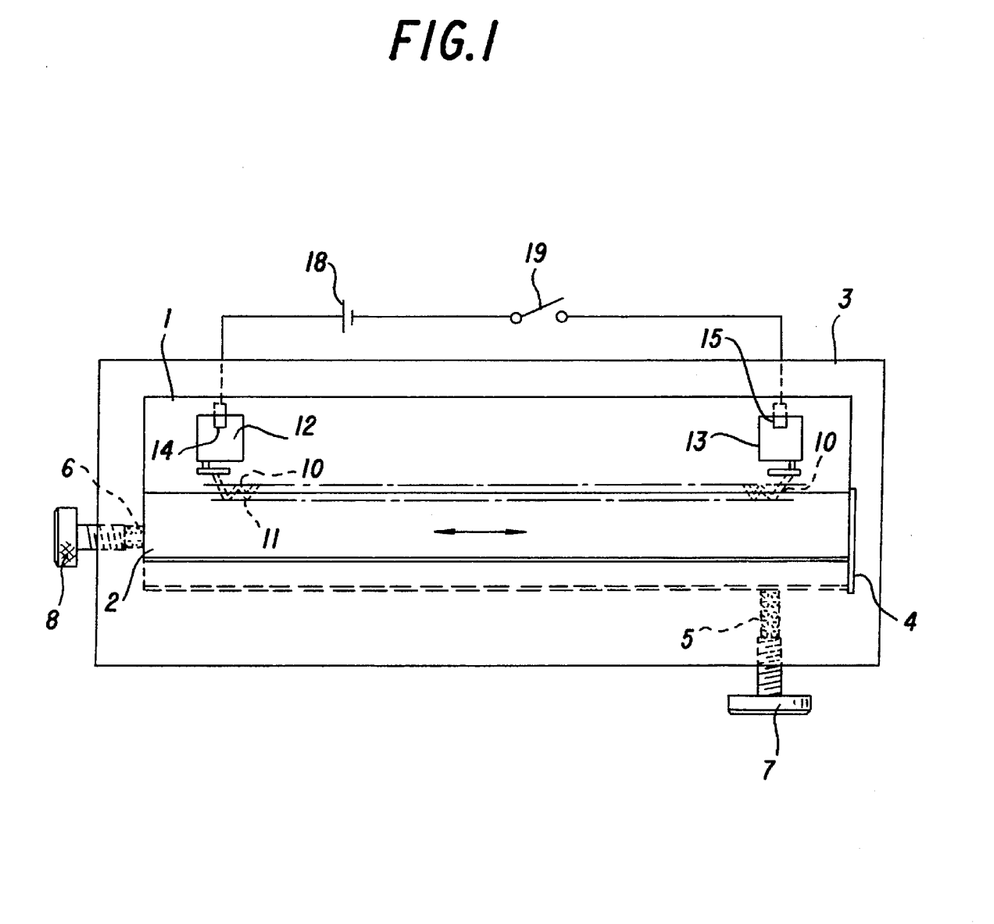
FIG. 1 is a plan of one form of the electrophoresis fractionator of the present invention.

In the electrophoresis fractionator of the present invention shown in FIG. 1, a stator 1 and a slider 2, forming the required two members, consist of respective rectangular parallelepiped blocks and fitted in a state of close contact with each other in a supporting frame 3. The above stator 1 and slider 2 are each preferably made of a colorless transparent material the inside of which can be viewed from the outside, such as an acrylic resin or a quartz glass.

While the stator 1 is firmly fixed in the frame 3, the slider 2 is slid along the longitudinal direction by removing a spacer 4 interposed between one longitudinal end of the slider 2 and the frame 3. The slide 2 is pressed against the stator 1 so as to come into close contact therewith by means of a spring 5 held by a screw 7 threaded into the frame 3. Further, in the longitudinal direction, the slider 2 is pressed against the spacer 4 by means of a spring 6 held by a screw 8 threaded into the frame 3.

A multiplicity of cells 10 each bent so as to have an inverted V shape are formed at constant pitches along the longitudinal direction in the surface of the stator 1 in contact with the surface of the slider 2, and a multiplicity of cells 11 each bent so as to have a V shape are formed at the same constant pitches along the longitudinal direction in the surface of the slider 2 in contact with the surface of the stator 1. The sizes of the cells 10, 11 may be arbitrary. It is preferred however that the full length, the cross-sectional diameter and included vertex angle of the V shape be about 10 mm, 1.5 mm and 60°, respectively.

The stator 1 is provided on both longitudinal ends thereof with reservoirs 12, 13 in such a manner that they are open to the upper surface of the stator 1, and therefore the reservoirs 12, 13 communicate with the respective outermost cells 10, 10 respectively positioned at both ends of the stator 1. An electrode 14 (positive electrode) and an electrode 15 (negative electrode) are disposed in the reservoirs 12, 13, respectively, and a direct current power source (battery) 18 is connected to both of the electrodes 14, 15 via a switch 19.

Figure 2A:
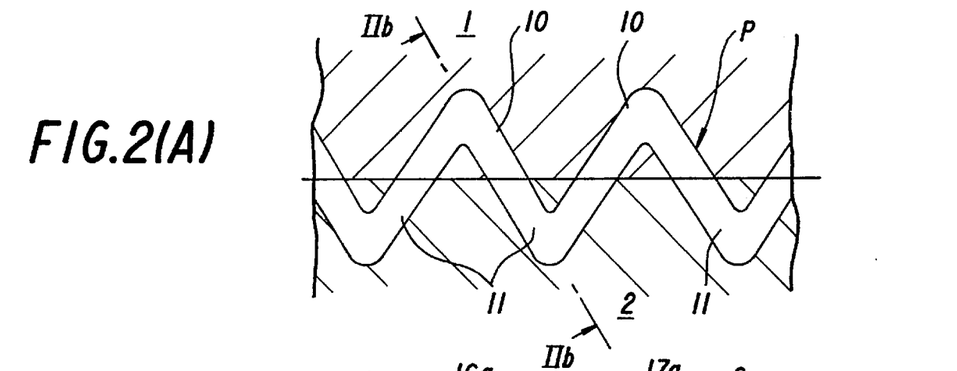
FIG. 2A is a cross section showing the state of a single zigzag electrophoresis passage being formed by a multiplicity of cells inside the electrophoresis fractionator of FIG. 1.
Figure 2B:
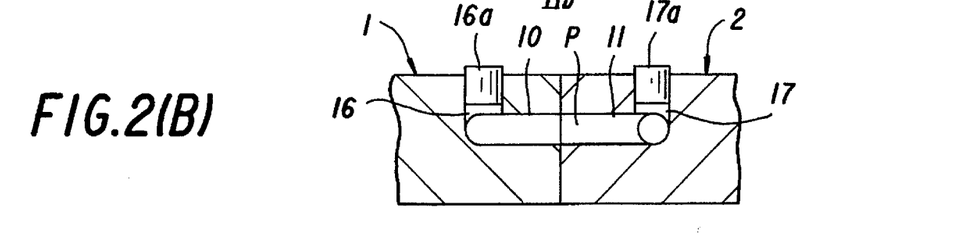
FIG. 2B is a sectional view taken in the direction of the arrows along the line IIb—IIb of FIG. 2A.
Figure 3A:
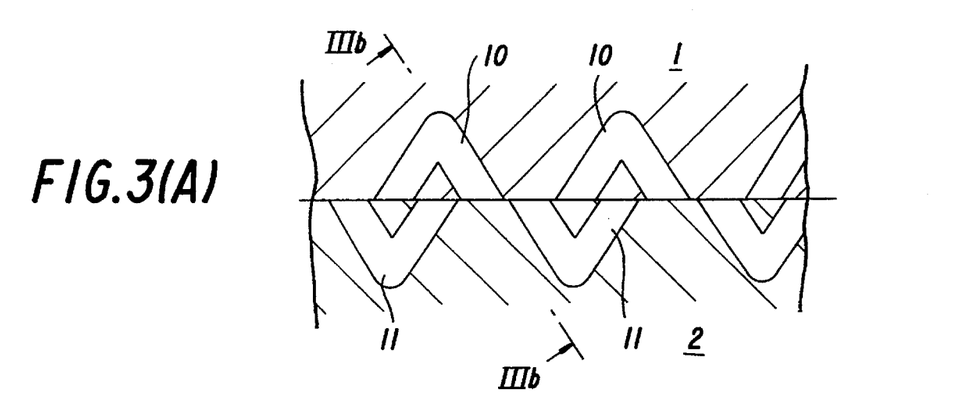
FIG. 3A is a cross section showing the state of the zigzag electrophoresis passage of FIG. 2A being separated into a plurality of cells separated from one another.
Figure 3B:
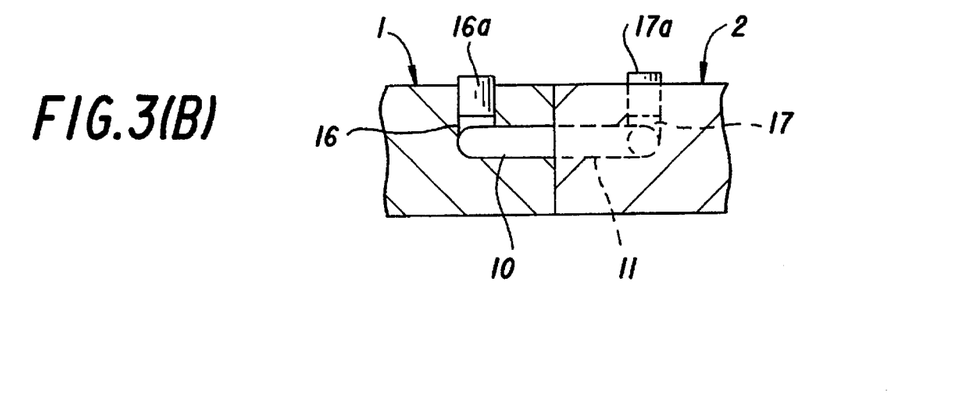
FIG. 3B is a sectional view taken in the direction of the arrows along the line IIIb—IIIb of FIG. 3A.

When the spacer 4 is interposed in the electrophoresis fractionator, the cells 10 of the stator 1 and the cells 11 of the slider 2 are alternately connected to each other to thereby form a single zigzag electrophoresis passage P as shown in FIGS. 2A and 2B. However, when the spacer 4 is removed to thereby slide the slider 2 along the longitudinal direction thereof, the cells 10, 11 are separated from each other to thereby switch the apparatus to the state of the several cells being independent from one another as shown in FIGS. 3A and 3B.

Further, upon movement of this slider 2 to disengage the several cells 10, 11 holes 16, 17 are created connecting the cells 10, 11, respectively, in such a manner that they open at the upper surfaces of the stator 1 and slider 2, respectively. According to necessity, plugs 16a, 17a are detachably fitted to the fractionation holes 16, 17, respectively. Thus, the substance fractionated by electrophoresis can be easily isolated and recovered from each cell, respectively, through the fractionation holes 16, 17 by means of a pipette or the like.

When, for example, a protein is desired to be fractionated and isolated, by the use of the above electrophoresis fractionator of the present invention, first, the multiplicity of cells 10 of the stator 1 and the multiplicity of cells 11 of the slider 2 are alternately connected to each other to thereby form a single zigzag electrophoresis passage P as shown in FIGS. 2A and 2B. Subsequently, this electrophoresis passage P is filled with an electrophoresis solution (carrier ampholyte) containing a single or a plurality of types of proteins or other molecules, and an alkali solution and an acid solution are filled into the reservoirs 12 and 13, respectively. When the electrophoresis passage P filled with the protein-containing electrophoresis solution is electrified by means of the electrode (positive electrode) 14 and the electrode (negative electrode) 15, a pH gradient is formed in the solution between the positive and negative electrodes. The proteins are thereby transported and focused at the respective corresponding isoelectric pHs along the pH gradient.

The electrophoresis is performed at a constant voltage, and the time at which the current has become constant is defined as the electrophoresis completion point. The higher the voltage, the shorter the electrophoresis time. When, however, the electrophoresis voltage is high from the beginning bubbling occurs to thereby deteriorate the fractionation accuracy. Therefore, the electrification is preferably conducted for a given period of time in the beginning at such a low voltage as will not cause bubbling, followed by switching to a high voltage for a further time with the result that stable electrophoresis can be accomplished within a short period of time.

When the slider 2 is moved along the longitudinal direction thereof immediately upon arrival of the current at a constant value by the above electrophoresis operation, the continuous electrophoresis passage P is interrupted by longitudinally moving the slider 2 whereby switching it to a plurality of cells 10, 11 separated from one another as shown in FIGS. 3A and 3B. The slider 2 should be moved to disrupt the single passage while continuing the electrification. If the electrification is terminated prior to the movement of the slider 2, the separation pattern formed by the electrophoresis collapses, so that separation of the molecules with high accuracy becomes unfeasible. After the above switching of the cells 10, 11 to the state of being separated from one another, the fractionated proteins are isolated in each cell 10, 11 and are recovered by means of a pipette or the like through the fractionation holes 16, 17 fitted to the respective cells 10, 11.

In the electrophoresis fractionator of the present invention, as mentioned above, the condition during electrophoresis operation is such that a plurality of cells are connected together to form a single electrophoresis passage P, but after arrival of the current at a constant value which indicates stabilized separation pattern, the two members are moved relative to each other with the result that the above plurality of cells are separated from one another. Therefore, the patterns separated by electrophoresis are never disordered to thereby enable fractionation with high accuracy. Further, the substance fractionated by electrophoresis can be accurately isolated by a simple operation of merely moving the two members relative to each other. Still further, the above procedure can be carried out irrespective of the size of the diameter of the electrophoresis passage, so that a large amount of sample can be treated at once.

The above electrophoresis fractionator of the present invention can be modified as follows.

Figure 4A:
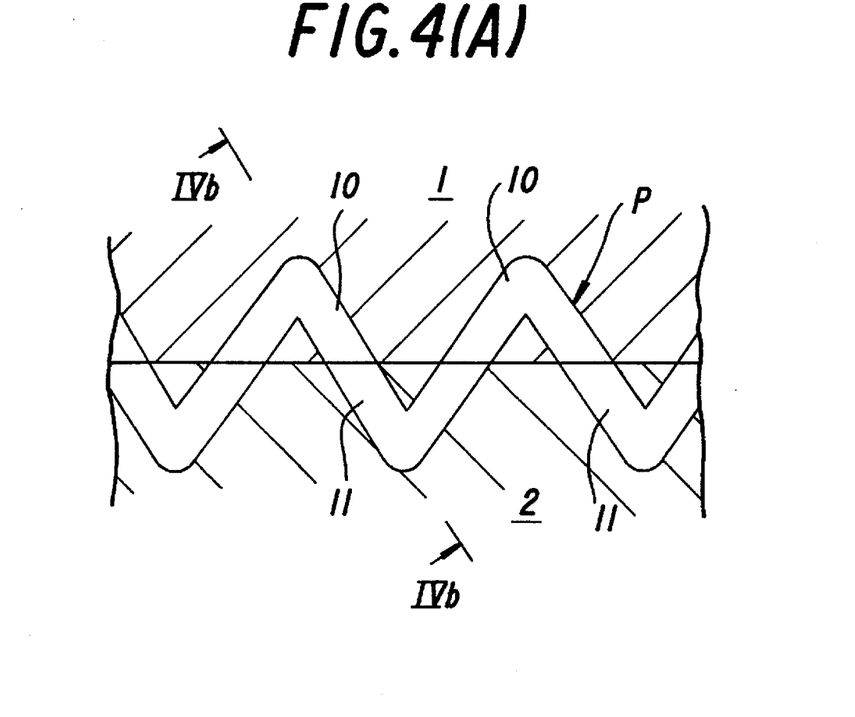
FIG. 4A is a cross section showing one embodiment in which each of the cells of the electrophoresis fractionator of FIG. 1 has been enlarged in the direction of its depth as in FIG. 4B.
Figure 4B:
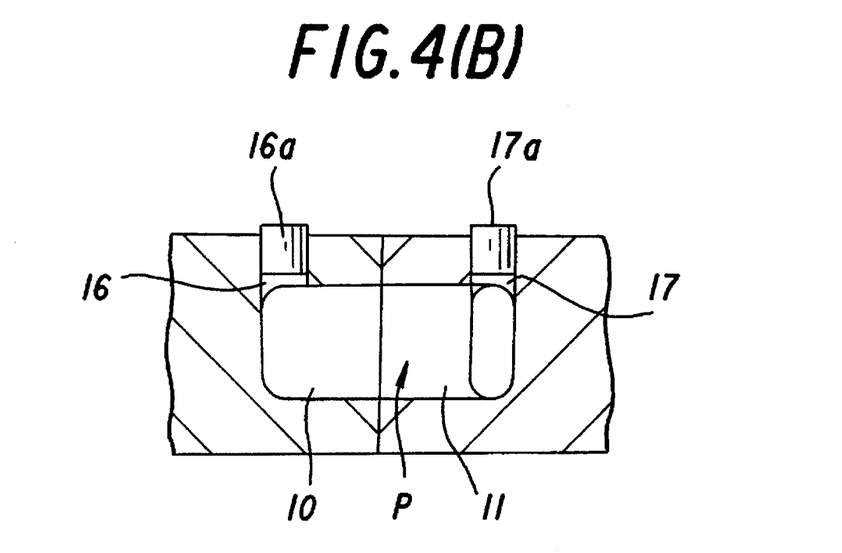
FIG. 4B is a sectional view taken in the direction of the arrows along the line IVb—IVb of FIG. 4A.

FIGS. 4A and 4B show another embodiment in which the volume of each cell can be enlarged without changing the number of divided cells 10, 11. More specifically, the sectional area of each cell is enlarged by increasing its depth without changing the inter-cell pitches. This enlargement of the cell volume enables an increase in the amount of sample which can be treated at once.

Figure 5A:
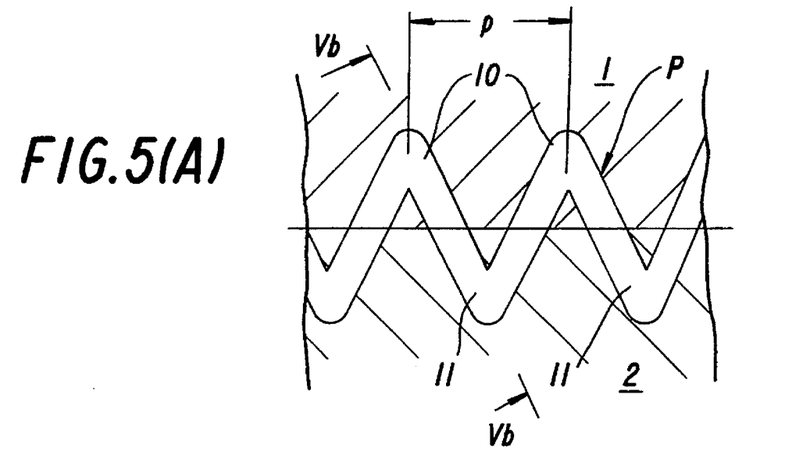
FIG. 5A is a cross section showing another embodiment in which the cells forming the zigzag electrophoresis passage have respective pitches decreased.
Figure 5B:
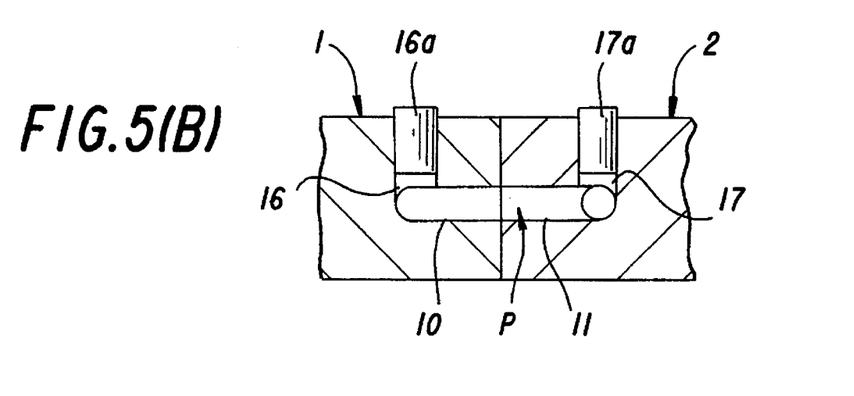
FIG. 5B is a sectional view taken in the direction of the arrows along the line Vb—Vb of FIG. 5A.

FIGS. 5A and 5B show a further embodiment in which the dividing pitch p of the cells 10, 11 is shortened to thereby increase the number of divided cells so as to improve the separative power of the electrophoresis fractionator.

Figure 6:
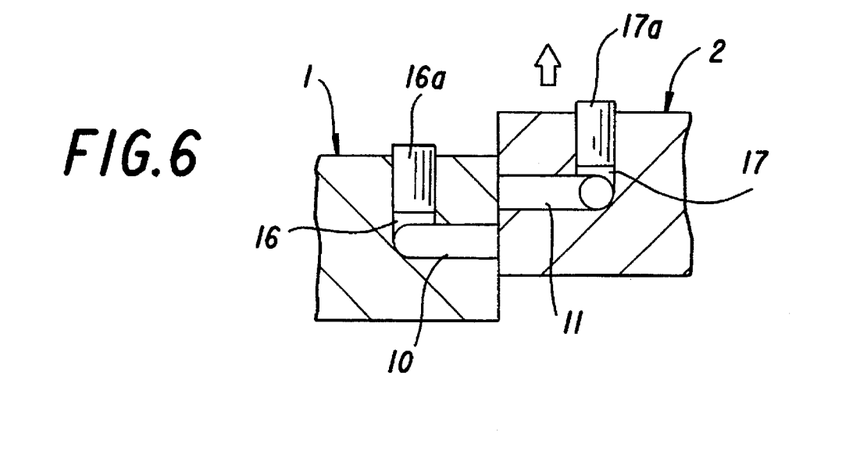
FIG. 6 is a longitudinal section showing the state of the zigzag electrophoresis passage of FIG. 2A being separated into a plurality of cells separated from one another by vertically moving the slider situated as in FIGS. 5A and 5B.

In this embodiment, the dividing pitch p of the cells 10, 11 is too small to attain separation of the cells 10, 11 from one another by sliding the slider 2 along the longitudinal direction thereof. Thus, in this embodiment, the slider 2 moved in the transverse direction, that is a direction crossing the longitudinal direction, i.e., the direction crossing the longitudinal direction as shown in FIG. 6, so that the cells 10, 11 are separated from one another.

Figure 7:
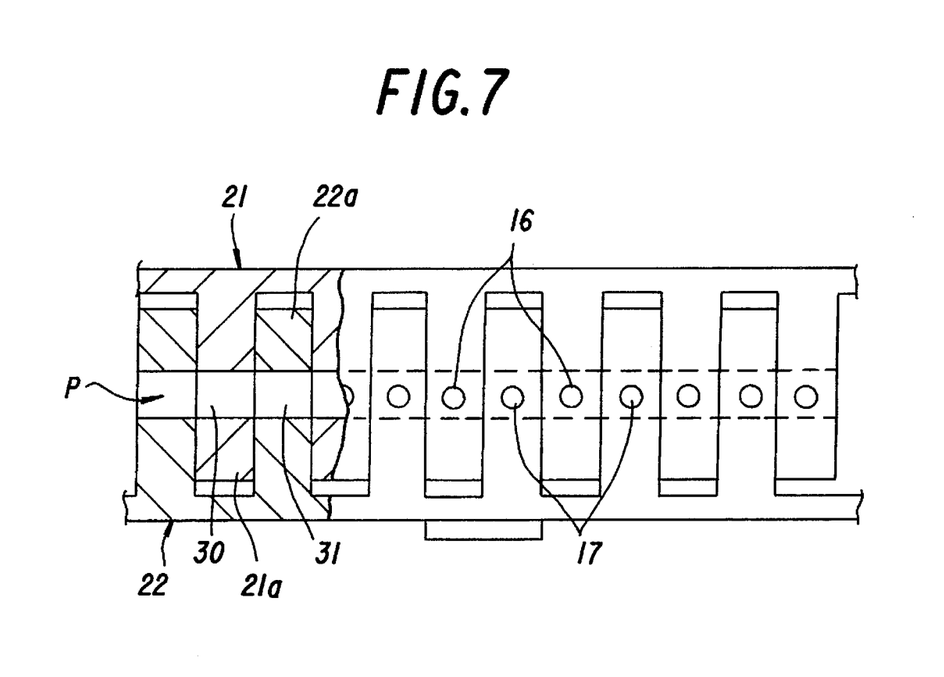
FIG. 7 is a partially sectional plan of an essential part of the electrophoresis fractionator according to a further embodiment of the present invention.
Figure 8:
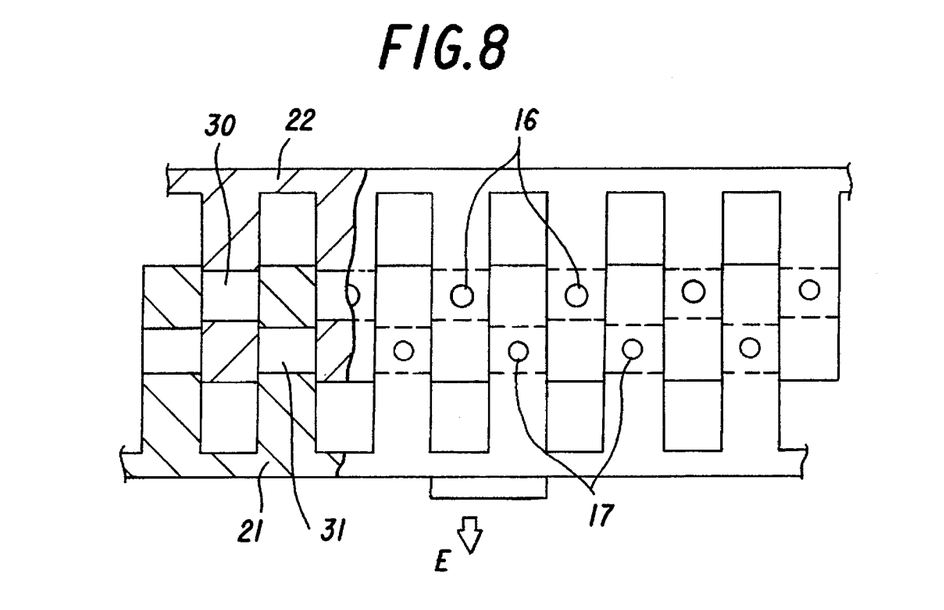
FIG. 8 is a partially sectional plan showing the state of the single electrophoresis passage of the electrophoresis fractionator of FIG. 7 being converted into a plurality of cells separated from one another.

FIGS. 7 and 8 show a still further embodiment of the present invention.

In this embodiment, the members constituting the stator 21 and slider 22 have respective multiplicities of laminates 21a, 22a. These laminates 21a, 22a are provided with respective cells 30, 31 each formed of a through hole. Further, these cells 30, 31 are provided with respective fractionation holes 16, 17.

The stator 21 and slider 22 are interlocked with each other in such a fashion that the respective laminates 21a, 22a are overlapped with one another, so that alternate switching is possible between a position where the cells 30 of the stator 21 and the cells 31 of the slider 22 are alternately connected to each other to form a single linear electrophoresis passage P as shown in FIG. 7 and a position where the cells 30 of the stator 21 and the cells 31 of the slider 22 are separated from one another as a result of the movement of the slider 22 in the arrowed direction as shown in FIG. 8. Therefore, the electrophoresis fractionator of this embodiment can perform the same electrophoresis fractionation and isolation as in the above embodiments.

Figure 9A:
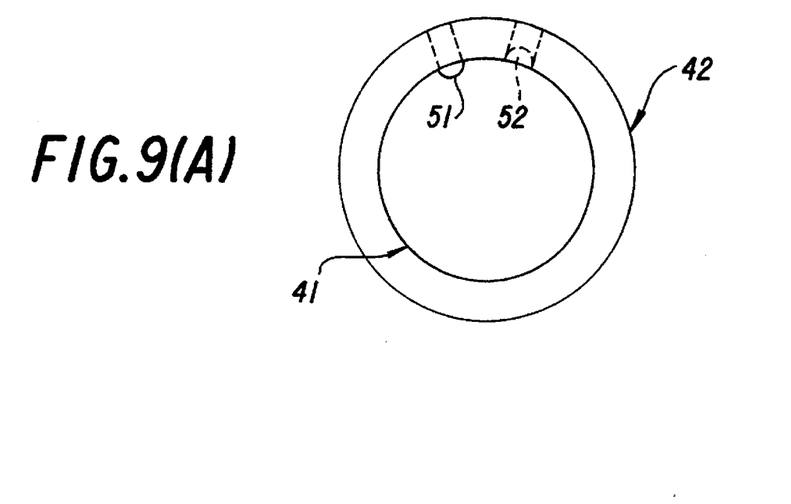
FIG. 9A is a front view of an essential part of the electrophoresis fractionator according to a still further embodiment of the present invention.
Figure 9B:
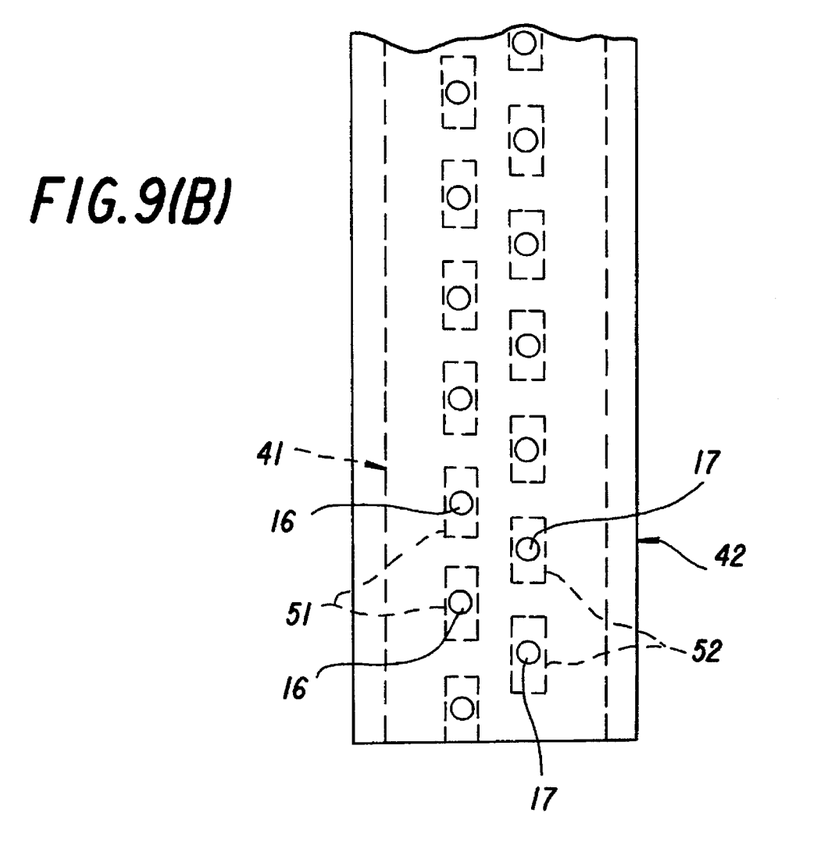
FIG. 9B is a plan of the essential part of the electrophoresis fractionating shown in FIG. 9A.

FIGS. 9A and 9B show still a further embodiment of the present invention.

In this embodiment, the members constituting the stator 42 and slider 41 are composed of a cylindrical body 41 and a rodlike body 42 fitted therein, respectively. The stator 42 (the cylindrical body) has a plurality of groove-shaped cells 52 provided along the longitudinal direction thereof at constant pitches on its inner circumferential surface in contact with the slider 41 of the rodlike body. On the other hand, the slider 41 has a plurality of groove-shaped cells 51 provided along the longitudinal direction thereof at the same constant pitches on its outer circumferential surface in contact with the stator 42 so as to be offset with respect to the cells 52. These cells 50, 51 are provided with respective fractionation holes 16, 17 which communicate with the outside.

In the use of the above stator 42 and slider 41, alternate switching is possible between a position where the cells 52, 51 are separated from one another and a position where a single electrophoresis passage is formed as a result of the movement of the slider 41 in the circumferential direction as shown in FIGS. 9A and 9B. Therefore, the electrophoresis fractionator of this embodiment can perform the same electrophoresis fractionation and isolation as in the above embodiments.

As described above, in the electrophoresis fractionator of the present invention, two members having a multiplicity of separate cells, formed in each of their surfaces in contact with each other, are adapted to move relative to each other to thereby enable alternate switching between a position where the above cells are connected together to form a single electrophoresis passage and a position where the cells are separated from one another to disconnect the electrophoresis passage. Therefore, the substance which has been separated and resolved by electrophoresis in the continuous passage can be isolated with high accuracy in the disconnected cells. This is accomplished by carrying out electrophoresis in the state of the multiplicity of the cells forming a single electrophoresis passage and then switching the positions of the cells to form separate cells. A large amount of sample can be treated at once.

Moreover, a fractionation with improved separative accuracy is possible by the use of the electrophoresis fractionator of the present invention in combination with chromatography of the contents of one or more separated cells, by which the fractions isolated by the electrophoresis fractionator can be further resolved and separated.

EXAMPLE 1

An electrophoresis fractionator having the structure shown in FIG. 1 was fabricated in which the cells provided in the stator and the slider totaled 61. With the use of this electrophoresis fractionator, electrophoresis fractionation of a commercially available mixture of albumin and myoglobin as standard proteins was conducted under the conditions specified below.

As a result, the albumin and myoglobin were separated from each other into about three fractions, thereby realizing fractionation with high accuracy.

Conditions electrophoresis solution:
   solution obtained by adding 0.001% bromophenol blue as a colorant to 4% Ampholine, electrode bath fluid:
   0.1 mol $H_3PO_4$ on the side of the positive electrode
   0.4 mol NaOH on the side of the negative electrode, voltage:
   300 V for 12 hr and 500 V for 24 hr, and sample:
   1 mg each of albumin and myoglobin (each obtained by separating a commercially available product with the use of ion-exchange HPLC and purifying the resultant sample to exhibit a single peak).

EXAMPLE 2

With the use of the same electrophoresis fractionator as in Example 1, electrophoresis fractionation of unpurified commercially available myoglobin as a sample, in an attempt to separate proteins having isoelectric points close to each other, was carried out under the conditions specified below. As a result, the originally fed myoglobin sample could be separated into three bands.

Conditions electrophoresis solution:
   solution obtained by adding 1% hydroxypropylmethylcellulose (HPMC) to 4% Ampholine for thickening the same, electrode bath fluid:
   0.1 mol $H_3PO_4$ on the side of the positive electrode
   0.4 mol NaOH on the side of the negative electrode, voltage:
   300 V for 12 hr and 500 V for 24 hr, and sample:
   1 mg of myoglobin (unpurified commercially available product).

EXAMPLE 3

With the use of the same electrophoresis fractionator as in Example 1, electrophoresis fractionation of a mixture of 1 mg each of α1-antitrypsin, albumin, transferrin and myoglobin as a sample was performed under the conditions I specified below, thereby achieving fractionation into 61 fractions.

Subsequently, each of the isolated 61 sample fractions was mounted on an autosampler and further separated by liquid chromatography under the conditions II specified below. The eluate from the column was continuously fractionated and detected for 1 min, and separation with high accuracy into 671 (11×61=671) fractions was achieved under the condition of one cycle of 11 min.

Conditions I electrophoresis solution:
   solution obtained by adding 1% hydroxypropylmethylcellulose (HPMC) to 4% Ampholine for thickening the same, electrode bath fluid:
   0.1 mol $H_3PO_4$ on the side of the positive electrode
   0.4 mol NaOH on the side of the negative electrode, voltage:
   300 V for 12 hr and 500 V for 24 hr, and sample:
   1 mg each of α1-antitrypsin, albumin, transferrin and myoglobin.

Condition II column:
   POROS R/M (4.6 in diameter ×100 mm, produced by Perseptive Biosystems), column temperature: 30° C., eluent:
   10 min gradient from 25% $CH_3CN$-0.1% THF to 55% $CH_3CN$-0.1% THF, flow rate: 3 ml/min, and detection: 280 nm.

Industrial Applicability

The electrophoresis fractionator of the present invention can be utilized in electrophoresis fractionation of charged substances such as proteins. Further, even when the substances to be subjected to electrophoresis fractionation are non-charged organic substances, the electrophoresis fractionator of the present invention can be utilized by adding a charged material, such as a surfactant, to each electrolytic solution to thereby bring the whole into a charged state.

Still further, the present invention is also applicable to cell fractionation and DNA (deoxyribonucleic acid) separation.

What is claimed is:

1. An electrophoresis fractionator comprising a multiplicity of separate cells provided on respective contact surfaces of two members, said members being in contact with each other movably relative to each other and adapted to move relative to each other to enable alternate switching between a position where the multiplicity of cells are connected together to form a single electrophoresis passage and a position where the multiplicity of cells are separated from one another, and electrodes provided on both respective ends of the electrophoresis passage formed to be single.

2. The electrophoresis fractionator according to claim 1, wherein each of the cells is provided with a fractionation hole.

3. The electrophoresis fractionator according to claim 2, wherein each of the cells has a bent form, so that the single electrophoresis passage is zigzagged when the two members is moved relative to each other up to a position where the multiplicity of cells are connected together to form a single electrophoresis passage.

4. The electrophoresis fractionator according to claim 2, wherein the two members have the respective forms of blocks whose mutual contact surfaces are individually planar.

5. The electrophoresis fractionator according to claim 2, wherein the two members have respective multiplicities of comb shaped laminates, each having a through hole as the cell, and wherein the two members are interlocked with each other in such a fashion that the respective laminates are overlapped with one another and movable relative to each other to enable alternate switching between a position where the through holes respectively provided in the laminates as the cells are connected together to form a single electrophoresis passage and a position where the cells are separated from one another.

6. The electrophoresis fractionator according to claim 2, wherein the two members are composed of the one having an inner circumferential surface and the other having an outer circumferential surface as the contact surfaces to be brought into contact with each other, these members being movable relative to each other in the circumferential direction.

7. The electrophoresis fractionator according to any of claims 1 to 6, wherein the substance fractionated by electrophoresis is any of proteins, DNAs and biological cells.

* * * * *